(12) United States Patent
Ordway et al.

(10) Patent No.: US 10,123,495 B2
(45) Date of Patent: Nov. 13, 2018

(54) CONTROLLED SYSTEM FOR SUPPORTING ALGAE GROWTH WITH ADSORBED CARBON DIOXIDE

(71) Applicant: GENERAL ATOMICS, San Diego, CA (US)

(72) Inventors: David W. Ordway, Poway, CA (US); David A. Hazlebeck, El Cajon, CA (US)

(73) Assignee: GENERAL ATOMICS, San Diego, CA (US)

(*) Notice: Subject to any disclaimer, the term of this patent is extended or adjusted under 35 U.S.C. 154(b) by 688 days.

(21) Appl. No.: 14/596,451

(22) Filed: Jan. 14, 2015

(65) Prior Publication Data

US 2015/0173317 A1 Jun. 25, 2015

Related U.S. Application Data

(63) Continuation-in-part of application No. 12/817,043, filed on Jun. 16, 2010, now abandoned.

(51) Int. Cl.
*C12M 1/04* (2006.01)
*A01G 33/00* (2006.01)
(Continued)

(52) U.S. Cl.
CPC .............. *A01G 33/00* (2013.01); *B01D 53/14* (2013.01); *C12M 21/02* (2013.01); *C12M 41/32* (2013.01);
(Continued)

(58) Field of Classification Search
CPC ...... C12M 21/02; C12M 21/12; C12M 41/32; C12M 41/34; C12M 41/48; A01G 33/00
See application file for complete search history.

(56) References Cited

U.S. PATENT DOCUMENTS 2,205,962 A * 6/1940 Reich ...................... C01B 31/20
423/232
2,732,663 A 1/1956 Dewey, II
(Continued)

FOREIGN PATENT DOCUMENTS

WO 2010002745 A1 1/2010
WO 2010138571 A1 12/2010
(Continued)

OTHER PUBLICATIONS

Barbosa, et al., Optimisation of Cultivation Parameters in Photobioreactors for Microalgae Cultivation Using the A-stat Technique, Biomolecular Engineering 20 (2003), pp. 115-123, Elsevier Science B.V.
(Continued)

*Primary Examiner* — William H. Beisner
(74) *Attorney, Agent, or Firm* — Nydegger & Associates

(57) ABSTRACT

A system and method for creating a useful carbon-enriched media in a reactor which will assimilate carbon into an algae biomass, requires measuring a respective carbon concentration of the media, $C_{(measured)}$, as it enters, and as it leaves the reactor. Operationally, desired carbon concentration values are preset, $C_{(set)}$, and are provided along with values obtained for $C_{(measured)}$ as input to a system controller. Respective differentials between $C_{(measured)}$ and $C_{(set)}$ at the reactor's input and output ports are determined by the controller and are used to control a volumetric fluid flow rate of the media through the reactor. Specifically, the controller establishes a volumetric fluid flow rate of the media as it is passed through an absorber where the media is carbon-enriched by interaction with combustion gases from an external source (e.g. a power plant).

8 Claims, 2 Drawing Sheets

(51) Int. Cl.
  *B01D 53/14* (2006.01)
  *C12M 1/34* (2006.01)
  *C12M 1/00* (2006.01)
  *C12M 1/36* (2006.01)

(52) U.S. Cl.
  CPC ............ *C12M 41/34* (2013.01); *C12M 41/48* (2013.01); *Y02A 40/88* (2018.01); *Y02E 50/343* (2013.01)

(56) References Cited

U.S. PATENT DOCUMENTS

| | | | |
|---|---|---|---|
| 2,854,792 A | 10/1958 | Juda | |
| 2,949,700 A | 8/1960 | Kathrein | |
| 3,195,271 A | 7/1965 | Golueke et al. | |
| 3,218,758 A | 11/1965 | Konikoff | |
| 3,468,057 A | 9/1969 | Buisson et al. | |
| 3,489,506 A * | 1/1970 | Galstaun | B01D 11/0488 261/113 |
| 3,521,400 A | 7/1970 | Ort | |
| 3,958,364 A | 5/1976 | Schenck et al. | |
| 4,087,936 A | 5/1978 | Savins et al. | |
| 4,236,349 A | 12/1980 | Ramus | |
| 4,253,271 A | 3/1981 | Raymond | |
| 4,391,887 A | 7/1983 | Baumgarten | |
| 4,417,415 A | 11/1983 | Cysewski et al. | |
| 4,958,460 A | 9/1990 | Nielson et al. | |
| 5,116,506 A | 5/1992 | Williamson et al. | |
| 5,330,913 A | 7/1994 | Nakayama | |
| 5,522,985 A | 6/1996 | Bender | |
| 5,659,977 A * | 8/1997 | Jensen | A01G 33/00 34/547 |
| 5,843,762 A | 12/1998 | Moll | |
| 6,000,551 A | 12/1999 | Kanel et al. | |
| 6,395,521 B1 | 5/2002 | Miura | |
| 6,524,486 B2 | 2/2003 | Borodyanski et al. | |
| 7,638,314 B2 | 12/2009 | Zappi | |
| 7,662,616 B2 | 2/2010 | Hazlebeck et al. | |
| 7,687,261 B2 | 3/2010 | Hazlebeck et al. | |
| 7,763,457 B2 | 7/2010 | Dunlop et al. | |
| 2005/0112735 A1 | 5/2005 | Zappi et al. | |
| 2006/0051274 A1 | 3/2006 | Wright et al. | |
| 2007/0048848 A1 | 3/2007 | Sears | |
| 2007/0048859 A1 | 3/2007 | Sears | |
| 2008/0009055 A1 | 1/2008 | Lewnard | |
| 2008/0086937 A1 | 4/2008 | Hazlebeck et al. | |
| 2008/0086938 A1 | 4/2008 | Hazlebeck et al. | |
| 2008/0087165 A1 | 4/2008 | Wright et al. | |
| 2008/0133039 A1 | 6/2008 | Brown | |
| 2008/0299643 A1 | 12/2008 | Howard et al. | |
| 2009/0081743 A1 | 3/2009 | Hazelbeck et al. | |
| 2009/0081748 A1 | 3/2009 | Oyler | |
| 2010/0120104 A1 | 5/2010 | Reed | |
| 2013/0217082 A1 | 8/2013 | Hazlebeck | |

FOREIGN PATENT DOCUMENTS

| | | | |
|---|---|---|---|
| WO | 2011159568 A1 | 12/2011 | |
| WO | 2012109379 A2 | 8/2012 | |
| WO | WO 2012109379 A2 * | 8/2012 | ............ C12M 21/02 |

OTHER PUBLICATIONS

Medina, et al., Downstream Processing of Algal Polyunsaturated Fatty Acids, Biotechnology Advances, vol. 16, No. 3, pp. 517-580, 1998, Elsevier Science Inc., USA.

Miao, et al., Biodiesel Production from Heterotrophic Microalgal Oil, Bioresource Technology 97 (2006), pp. 841-846, Department of Biological Sciences and Biotechnology, Tsinghua University, Beijing 10084, PR China.

NIWA (National Institute of Water & Atmospheric Research), "Bio-oil from Wastewater Algae," online article published at www.niwa.co.nz, May 21, 2009.

Sheehan, et al., NREUTP-580-24190 A Look Back at the U.S. Department of Energy's Aquatic Species Program: Biodiesel from Algae, U.S. Department of Energy's Office of Fuels Development, Jul. 1998.

S. Heubeck and R. Craggs, "Resource Assessment of Algae Biomass for Potential Bio-Energy Production in New Zealand," New Zealand Forest Research Institute Limited, NIWA Client Report: HAM2007-157, Oct. 2007, NIWA Project: SCI08282, National Institute of Water & Atmospheric Research Ltd., Hamilton, New Zealand.

Spolaore, et al., Commercial Applications of Microalgae, Journal of Bioscience and Bioengineering, vol. 101, No. 2, 87-96, 2006, Laboratoire de Genie des Procedes et Materiaux, Ecole Centrale Paris, Paris, France.

European Search Report, European Patent Application 16150793.4, dated Jan. 11, 2016.

* cited by examiner

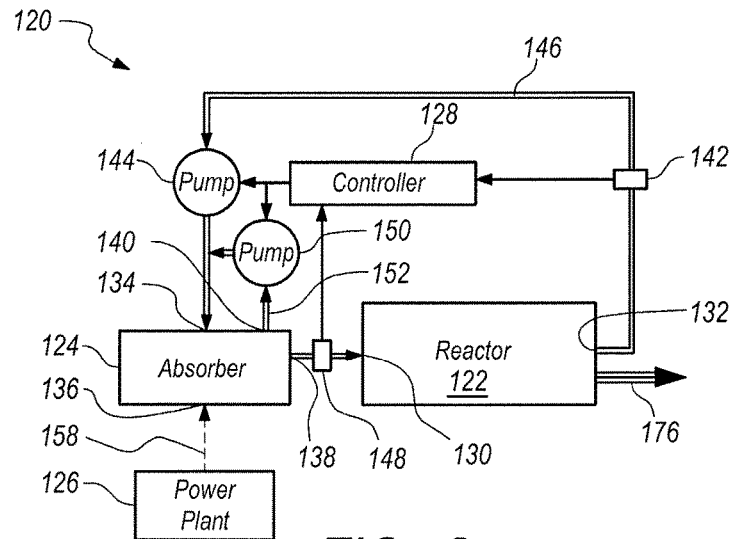
FIG. 3
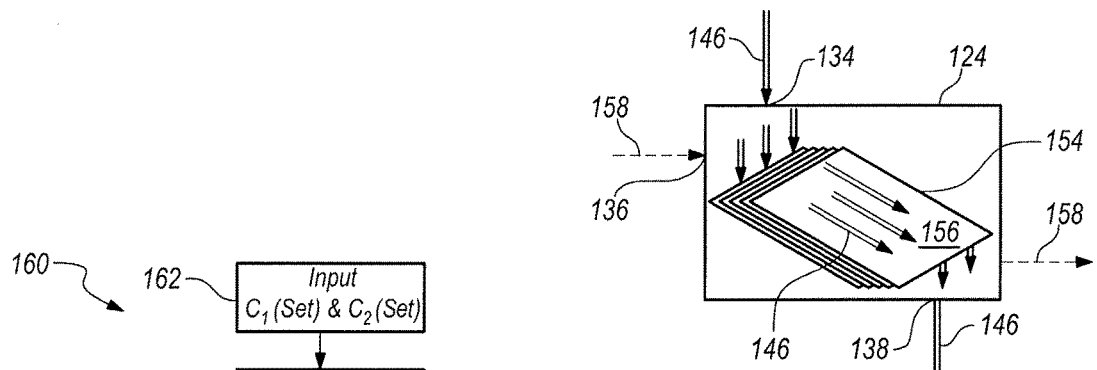
FIG. 4
FIG. 5
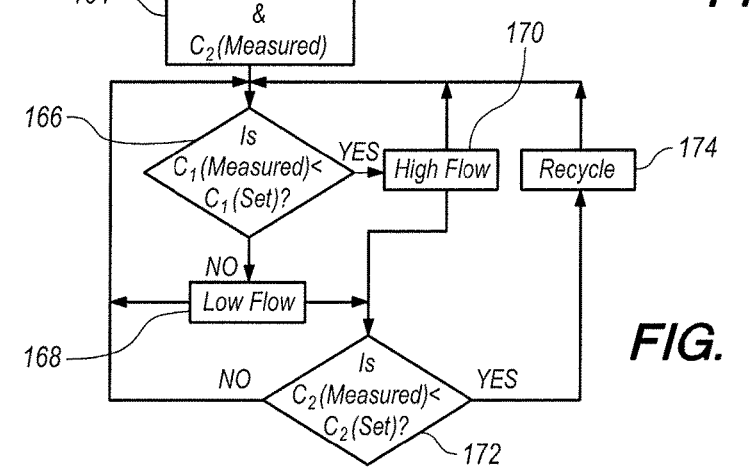

CONTROLLED SYSTEM FOR SUPPORTING ALGAE GROWTH WITH ADSORBED CARBON DIOXIDE

This application is a continuation-in-part of application Ser. No. 12/817,043, filed Jun. 16, 2010, which is currently pending. The contents of application Ser. No. 12/817,043 are incorporated herein by reference.

FIELD OF THE INVENTION

The present invention pertains generally to methods for growing algae. More particularly, the present invention pertains to the use of a medium for growing algae that is comprised of a solution containing carbon. The present invention is particularly, but not exclusively, useful as a system for supporting growth of algae with bicarbonate solution, and with charging used solution with adsorbed carbon dioxide at a liquid-gas contact medium for further support of algae growth.

BACKGROUND OF THE INVENTION

As worldwide petroleum deposits decrease, there is rising concern over petroleum shortages and the costs that are associated with the production of hydrocarbon products. As a result, alternatives to products that are currently processed from petroleum are being investigated. In this effort, biofuel, such as biodiesel, has been identified as a possible alternative to petroleum-based transportation fuels. In general, a biodiesel is a fuel comprised of mono-alkyl esters of long chain fatty acids derived from plant oils or animal fats. In industrial practice, biodiesel is created when plant oils or animal fats react with an alcohol, such as methanol.

For plant-derived biofuel, solar energy is first transformed into chemical energy through photosynthesis. The chemical energy is then refined into a usable fuel. Currently, the process involved in creating biofuel from plant oils is expensive relative to the process of extracting and refining petroleum. It is possible, however, that the cost of processing a plant-derived biofuel could be reduced by maximizing the rate of growth of the plant source. Because algae is known to be one of the most efficient plants for converting solar energy into cell growth, it is of particular interest as a biofuel source. Importantly, the use of algae as a biofuel source presents no exceptional problems, i.e., biofuel can be processed from oil in algae as easily as from oils in land-based plants.

While algae can efficiently transform solar energy into chemical energy via a high rate of cell growth, it has been difficult to create environments in which algae cell growth rates are optimized. Specifically, the conditions necessary to facilitate a fast growth rate for algae cells in large-scale operations have been found to be expensive to create. While sunlight can be cheaply and easily fed to algae, the other sources of growth may require expensive distribution systems. For instance, it may be difficult to provide carbon dioxide at the appropriate levels throughout a system. For commercial purposes, reliance on normal absorption of $CO_2$ from the atmosphere, such as at a pond-air interface, is too slow. On the other hand, conventional pumping techniques with extensive piping networks are too costly. Thus, an alternate source of $CO_2$ is required. One possible source of carbon dioxide is found in flue gases from power plants or other combustion sources. Further, the carbon dioxide in flue gases is generally treated as pollution. Therefore, using carbon dioxide from flue gases will help abate pollution.

A commercially viable source of $CO_2$ for algae photosynthesis is a bicarbonate solution. During this photosynthesis, it happens that a carbonate solution is generated. Further, it is known that such a carbonate solution will adsorb $CO_2$ from air (albeit somewhat inefficiently) for conversion back to a bicarbonate solution. Within this cycle, in a microalgae bioreactor system, the conversion from a bicarbonate solution to a carbonate solution is a consequence of algae growth. On the other hand, as mentioned above, the conversion from a carbonate solution (medium) to a bicarbonate solution can be accomplished merely by exposure to air. Also, in a situation where algae are being grown in a bioreactor system for the purpose of manufacturing a biodiesel fuel, $CO_2$ can be recovered from the power plant effluent to create a bicarbonate solution.

In light of the above, it is an object of the present invention to provide a controlled system for supporting the growth of algae which also reduces fossil fuel pollution. Another object of the present invention is to provide a system for growing algae which reduces input costs. Another object of the present invention is to control the adsorption of carbon dioxide at a liquid-gas contact medium into a solution for feeding algae. Another object of the present invention is to provide a system for growing algae that utilizes a bicarbonate solution to deliver carbon to the algae. Another object of the present invention is to replenish spent medium with carbon dioxide in order to support further growth of algae in the medium. Still another object of the present invention is to introduce a bicarbonate solution into an algae growth medium to establish elevated $CO_2$ levels in a bioreactor system for algae growth. Another object of the present invention is to recycle a carbonate solution from a bioreactor system for conversion to a bicarbonate solution for subsequent use in growing algae in the bioreactor system. Yet another object of the present invention is to provide a system and method for growing algae that is simple to implement, easy to use, and comparatively cost effective.

SUMMARY OF THE INVENTION

In accordance with the present invention, a system and method are provided for growing algae. Importantly, the system and method provide for the adsorption of carbon dioxide into the medium for supporting algae growth. Further, the system is able to use the carbon dioxide from flue gases or other pollution.

In the system, a channel holds bicarbonate solution to support algae growth. During growth, the algae uses carbon dioxide and converts the bicarbonate solution into carbonate solution. In order to reuse the solution, the system provides a high surface area gas-liquid contact medium. Specifically, the carbonate solution is delivered to and moves through the gas-liquid contact medium. At the same time, air including the carbon dioxide is moved across the contact medium. During contact between the gas and liquid, the carbonate solution adsorbs carbon dioxide from the air and is converted into bicarbonate solution. After this process is completed, the bicarbonate solution is returned to the channel to support further algae growth.

When used with a power plant, the system can be optimized by using steam power from the power plant for operation. Specifically, a fan using the steam power can direct the air across the contact medium. Further, the steam power can be used to move the solution to, from, and within the channel.

An important aspect of the present invention is its incorporation of a controller (i.e. a computer) that monitors and controls the carbon enrichment of an algae growth media in a reactor. For purposes of the present invention this reactor may be either a pond, a plug flow reactor, an expanding plug flow reactor, or any other type reactor that is useful for growing an algae biomass. Regardless of type, however, the controller provides control over carbon concentration levels for the growth media in the reactor. To do this, the reactor in which an algae biomass is to be grown is configured with sensors that detect the carbon concentration in the growth media as it enters the reactor, and as it exits the reactor. Optimally, the carbon concentration of growth media entering the reactor will be sufficiently carbon-enriched to maximize growth of an algae biomass as it is being processed in the reactor. A necessary consequence of this, however, is that the carbon concentration of growth media exiting the reactor should not already be completely depleted of carbon. Nevertheless, it should be relatively carbon-poor. In either event, it needs to be enriched before it is used as the growth media in a subsequent cycle.

As envisioned for the present invention, exhaust gases from a carbon-rich source, such as a power plant, are used to provide the carbon that is needed for enriching the post-cycle, carbon-poor algae growth media from the reactor before it is returned to the reactor as a carbon-enriched media. In this cycle, carbon concentration levels, both upstream and downstream from the reactor, are measured and respectively compared by the controller with preset carbon concentration levels that are identified for optimal system performance. Based on these comparisons, the volumetric flow rate of the media through an absorber, which provides carbon enrichment for the growth media, is controlled to achieve the optimal carbon concentrations.

Structurally, the reactor that is used for growing algae biomass in the media has an input port and an output port. Also included in the system is an absorber which includes a plurality of panels. Further, the absorber has a first input port, a second input port, a first output port and a second output port. Another important component of the system is a source of combustion gases having a conduit for directing the combustion gases into the absorber through its first input port.

Interconnecting components within the system include a pump for establishing a volumetric flow rate of carbon-poor media from the output port of the reactor and into the second input port of the absorber. As envisioned for the present invention, carbon-poor growth media from the reactor is presented on panel surface areas in the absorber for a counter current flow interaction with the combustion gases. It is this interaction that creates the carbon-enriched growth media for discharge from the first output port of the absorber. The carbon-enriched growth media is then introduced into the reactor through the input port of the reactor. Another structural component is a recycling pump for transferring media from the second output port of the absorber and back into the absorber via its second input port.

Control for the system is accomplished by the controller which requires a first sensor for measuring a first carbon concentration level, $C_{1(measured)}$, in the reactor. Specifically, $C_{1(measured)}$ is taken downstream from the reactor at or near the output port of the reactor. Also included is a second sensor for measuring a second carbon concentration level, $C_{2(measured)}$, of media entering the reactor. This is the same media that is discharged from the first output port of the absorber. The controller then operates the pump with input from the first and second sensors to establish an optimized assimilation of captured carbon from the carbon-enriched growth media into the algae biomass in the reactor.

In addition to taking carbon concentration measurements as disclosed above, a methodology for controlling the system of the present invention involves inputting the controller with a first preset carbon concentration $C_{1(set)}$ and a second preset carbon concentration $C_{2(set)}$. In detail the first preset carbon concentration $C_{1(set)}$ is based on an apparent carbon dioxide $CO_2$ concentration gradient which is determined by an interaction between aqueous media in the reactor and the atmosphere of the local environment of the reactor (e.g. bicarbonate, carbonic acid or carbon dioxide). Similarly, the second preset carbon concentration $C_{2(set)}$ is based on an apparent carbon dioxide $CO_2$ concentration gradient which is determined by an interaction between combustion gases and the relatively carbon-poor growth media that is introduced into the absorber.

For an operation of the present invention, the pump is activated by the controller to operate with a predetermined high fluid flow rate when $C_{1(measured)}$ is below $C_{1(set)}$. Alternatively, the high fluid flow rate can be employed when $C_{2(measured)}$ is below $C_{2(set)}$. On the other hand, the pump can be activated to operate with a predetermined low fluid flow rate when $C_{1(measured)}$ is above $C_{1(set)}$.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which:

FIG. 3 is a schematic presentation of operative components for controlling the carbon enrichment of a media for growing an algae biomass in a reactor;

FIG. 4 is a perspective schematic view of components for an exemplary absorber as envisioned for the present invention; and FIG. 5 is a decision flow chart for the operation of a system in accordance with the present invention.

DESCRIPTION OF THE PREFERRED EMBODIMENTS

Figure 1:
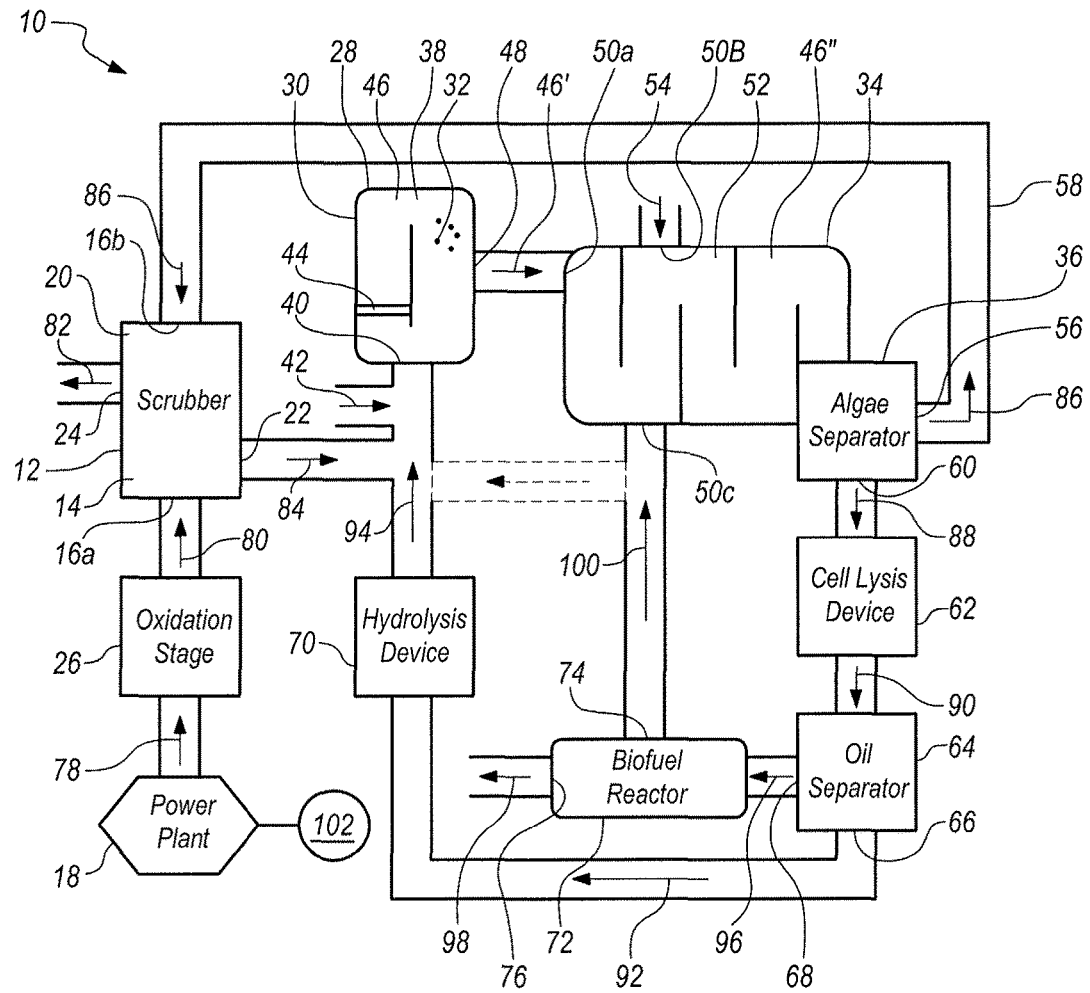
FIG. 1 is a schematic view of an algae growing system in accordance with the present invention.

Referring to FIG. 1, a system for producing biofuel from pollutant-fed algae is shown and generally designated 10. As shown, the system 10 includes a scrubber 12 for scrubbing a pollutant-contaminated fluid stream. Specifically, the scrubber 12 includes a chamber 14 and an input port 16a for receiving flue gas from a combustion source such as a power plant 18 and a scrubber solution 20. Typically, the flue gas includes pollutants such as carbon dioxide, sulfur oxides, and/or nitrogen oxides. Also, the scrubber solution 20 typically comprises sodium bicarbonate. As further shown, the scrubber 12 includes a solution outlet 22 and a gas outlet 24. Also, the system 10 includes an oxidation stage 26 for oxidizing pollutants in the flue gas to facilitate their removal from the flue gas. As shown, the oxidation stage 26 is interconnected between the power plant 18 and the scrubber 12.

As further shown, the system 10 includes a bioreactor 28 comprised of at least one chemostat 30 for growing algae cells (exemplary cells depicted at 32) and a plug flow reactor 34 for treating the algae cells 32 to trigger cell production of triglycerides. Preferably, and as shown, both the chemostat 30 and the plug flow reactor 34 are open raceways, though closed systems are also contemplated. Further, such open systems 10 can cover several acres of land to optimize economies of scale. For purposes of the present invention, the system 10 includes an algae separator 36 for removing the algae cells 32 from the plug flow reactor 34. As shown in FIG. 1, the chemostat 30 includes a channel 38. As further shown, the channel 38 is provided with an input port 40 that is in fluid communication with the solution outlet 22 of the scrubber chamber 14. For purposes of the present invention, the input port 40 is also in communication with a reservoir (not illustrated) holding a nutrient mix (indicated by arrow 42). Preferably, the nutrient mix 42 includes phosphorous, nitrogen, sulfur and numerous trace elements necessary to support algae growth that are not provided to the bioreactor 28 by the scrubber solution 20. Further, the chemostat 30 is provided with a paddlewheel 44 for causing the medium 46 formed by the scrubber solution 20 and the nutrient mix 42 to continuously circulate around the channel 38 at a predetermined fluid flow velocity. Also, each channel 38 is provided with an output port 48 in communication with the plug flow reactor 34.

As shown, the plug flow reactor 34 includes an input port 50a for receiving overflow medium (indicated by arrow 46') with algae cells 32 from the output port 48 of the chemostat 30. As further shown, the plug flow reactor 34 includes a channel 52 for passing the medium 46" with algae cells 32 downstream. The flow rate of the medium 46" is due solely to gravity and the force of the incoming overflow medium 46' from the chemostat 30. Preferably, the plug flow reactor 34 has a substantially fixed residence time of about one to four days. For purposes of the present invention, the system 10 is provided with a reservoir (not shown) that holds a modified nutrient mix (indicated by arrow 54). Further, the channel 52 is provided with an input port 50b for receiving the modified nutrient mix 54. In order to manipulate the cellular behavior of algae cells 32 within the plug flow reactor 34, the modified nutrient mix 54 may contain a limited amount of a selected constituent, such as nitrogen or phosphorous. For instance, the nutrient mix 54 may contain no nitrogen. Alternatively, the algae cells 32 may exhaust nutrients such as nitrogen or phosphorous in the nutrient mix 42 at a predetermined point in the plug flow reactor 34. By allowing such nutrients to be exhausted, desired behavior in the algae cells 32 can be caused without adding a specific modified nutrient mix 54. Further, simply water can be added through the modified nutrient mix 54 to compensate for evaporation. In addition to input ports 50a and 50b, the channel 52 is further provided with an input port 50c to receive other matter.

In FIG. 1, the algae separator 36 is shown in fluid communication with the channel 52 of the plug flow reactor 34. For purposes of the present invention, the algae separator 36 separates the algae cells 32 from the medium 46" and the remaining nutrients therein through flocculation and/or filtration. As further shown, the algae separator 36 includes an effluence outlet 56 and an algae cell outlet 60. For purposes of the present invention, the system 10 includes a channel 58 providing fluid communication between the effluence outlet 56 and the scrubber 12 through a solution input port 16b in the scrubber chamber 14.

Also, the system 10 includes a cell lysis apparatus 62 that receives algae cells 32 from the algae outlet 60 of the algae separator 36. As shown, the cell lysis apparatus 62 is in fluid communication with an oil separator 64. For purposes of the present invention, the oil separator 64 is provided with two outlets 66, 68. As shown, the outlet 66 is connected to a hydrolysis apparatus 70. Further, the hydrolysis apparatus 70 is connected to the input port 40 in the channel 38 of the chemostat 30.

Referring back to the oil separator 64, it can be seen that the outlet 68 is connected to a biofuel reactor 72. It is further shown that the biofuel reactor 72 includes two exits 74, 76. For purposes of the present invention, the exit 74 is connected to the input port 50c in the channel 52 of the plug flow reactor 34. Additionally or alternatively, the exit 74 may be connected to the input port 40 in the chemostat 30. Further, the exit 76 may be connected to a tank or reservoir (not shown) for purposes of the present invention.

In operation of the present invention, pollutant-contaminated flue gas (indicated by arrow 78) is directed from the power plant 18 to the oxidation stage 26. At the oxidation stage 26, nitrogen monoxide in the flue gas 78 is oxidized by nitric acid or by other catalytic or non-catalytic technologies to improve the efficiency of its subsequent removal. Specifically, nitrogen monoxide is oxidized to nitrogen dioxide. Thereafter, the oxidized flue gas (indicated by arrow 80) is delivered from the oxidation stage 26 to the scrubber 12. Specifically, the oxidized flue gas 80 enters the chamber 14 of the scrubber 12 through the input port 16a. Upon the entrance of the flue gas 80 into the chamber 14, the scrubber solution 20 is sprayed within the chamber 14 to absorb, adsorb or otherwise trap the pollutants in the flue gas 80 as is known in the field of scrubbing. With its pollutants removed, the clean flue gas (indicated by arrow 82) exits the scrubber 12 through the gas outlet 24. At the same time, the scrubber solution 20 and the pollutants exit the scrubber 12 through the solution outlet 22.

After exiting the scrubber 12, the scrubber solution 20 and pollutants (indicated by arrow 84) enter the chemostat 30 through the input port 40. Further, the nutrient mix 42 is fed to the chemostat 30 through the input port 40. In the channel 38 of the chemostat 30, the nutrient mix 42, scrubber solution 20 and pollutants (arrow 84) form the medium 46 for growing the algae cells 32. This medium 46 is circulated around the channel 38 by the paddlewheel 44. Further, the conditions in the channel 38 are maintained for maximum algal growth. For instance, in order to maintain the desired conditions, the medium 46 and the algae cells 32 are moved around the channel 38 at a preferred fluid flow velocity of approximately fifty centimeters per second. Further, the amount of algae cells 32 in the channel 38 is kept substantially constant. Specifically, the nutrient mix 42 and the scrubber solution 20 with pollutants (arrow 84) are continuously fed at selected rates into the channel 38 through the input port 40, and an overflow medium 46' containing algae cells 32 is continuously removed through the output port 48 of the channel 38.

After entering the input port 50a of the plug flow reactor 34, the medium 46" containing algae cells 32 moves downstream through the channel 52 in a plug flow regime. Further, as the medium 46" moves downstream, the modified nutrient mix 54 may be added to the channel 52 through the input port 50b. This modified nutrient mix 54 may contain a limited amount of a selected constituent, such as nitrogen or phosphorous. The absence or small amount of the selected constituent causes the algae cells 32 to focus on energy storage rather than growth. As a result, the algae cells 32 form triglycerides.

At the end of the channel 52, the algae separator 36 removes the algae cells 32 from the remaining effluent (indicated by arrow 86). Thereafter, the effluence 86 is discharged from the algae separator 36 through the effluence outlet 56. In order to recycle the effluence 86, it is delivered through channel 58 to the input port 16b of the scrubber 12 for reuse as the scrubber solution 20. Further, the removed algae cells (indicated by arrow 88) are delivered to the cell lysis apparatus 62. Specifically, the removed algae cells 88 pass out of the algae cell outlet 60 to the cell lysis apparatus 62. For purposes of the present invention, the cell lysis apparatus 62 lyses the removed algae cells 88 to unbind the oil therein from the remaining cell matter. After the lysing process occurs, the unbound oil and remaining cell matter, collectively identified by arrow 90, are transmitted to the oil separator 64. Thereafter, the oil separator 64 withdraws the oil from the remaining cell matter as is known in the art. After this separation is performed, the oil separator 64 discharges the remaining cell matter (identified by arrow 92) out of the outlet 66 of the oil separator 64 to the input port 40 of the chemostat 30.

In the chemostat 30, the remaining cell matter 92 is utilized as a source of nutrients and energy for the growth of algae cells 32. Because small units of the remaining cell matter 92 are more easily absorbed or otherwise processed by the growing algae cells 32, the remaining cell matter 92 may first be broken down before being fed into the input port 40 of the chemostat 30. To this end, the hydrolysis apparatus 70 is interconnected between the oil separator 64 and the chemostat 30. Accordingly, the hydrolysis apparatus 70 receives the remaining cell matter 92 from the oil separator 64, hydrolyzes the received cell matter 92, and then passes hydrolyzed cell matter (identified by arrow 94) to the chemostat 30.

Referring back to the oil separator 64, it is recalled that the remaining cell matter 92 was discharged through the outlet 66. At the same time, the oil withdrawn by the oil separator 64 is discharged through the outlet 68. Specifically, the oil (identified by arrow 96) is delivered to the biofuel reactor 72. In the biofuel reactor 72, the oil 96 is reacted with alcohol, such as methanol, to create mono-alkyl esters, i.e., biofuel fuel. This biofuel fuel (identified by arrow 98) is released from the exit 76 of the biofuel reactor 72 to a tank, reservoir, or pipeline (not shown) for use as fuel. In addition to the biofuel fuel 98, the reaction between the oil 96 and the alcohol produces glycerin as a byproduct. For purposes of the present invention, the glycerin (identified by arrow 100) is pumped out of the exit 74 of the biofuel reactor 72 to the input port 50c of the plug flow reactor 34.

In the plug flow reactor 34, the glycerin 100 is utilized as a source of carbon by the algae cells 32. Importantly, the glycerin 100 does not provide any nutrients that may be limited to induce oil production by the algae cells 32 or to trigger flocculation. The glycerin 100 may be added to the plug flow reactor 34 at night to aid in night-time oil production. Further, because glycerin 100 would otherwise provide bacteria and/or other non-photosynthetic organisms with an energy source, limiting the addition of glycerin 100 to the plug flow reactor 34 only at night allows the algae cells 32 to utilize the glycerin 100 without facilitating the growth of foreign organisms. As shown in FIG. 1, the exit 74 of the biofuel reactor 72 may also be in fluid communication with the input port 40 of the chemostat 30 (connection shown in phantom). This arrangement allows the glycerin 100 to be provided to the chemostat 30 as a carbon source. While FIG. 1 illustrates that a paddlewheel 44 or gravity for moving the medium 46 through the channels 38 and 52, steam power 102 from the power plant 18 may be used to power such movement.

Figure 2:
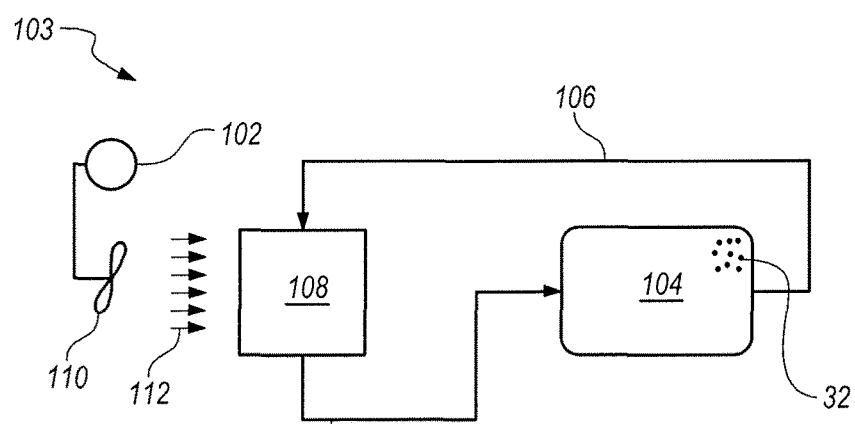
FIG. 2 is a schematic view of the conversion between carbonate and bicarbonate for the present invention.

In FIG. 2, a system for supporting algae growth with adsorbed carbon dioxide is illustrated and generally designated 103. In FIG. 2, the channels 38 and 52 are represented collectively by reference number 104. These channels 104 hold the medium 46 that includes bicarbonate solution. As algae 32 grows in the channels 104 it depletes the medium 46 of carbon and the medium 46 becomes principally carbonate solution. In order to replenish the carbonate solution, the system 103 provides for removal of the carbonate solution 106 from the channels 104. As shown, the carbonate solution 106 is delivered to a high surface area liquid-gas contact medium 108. As shown, a fan 110, powered by steam power 102, moves air 112 including carbon dioxide across the contact medium 108. As a result, when the carbonate solution 106 moves slowly across or drips through the contact medium 108, it adsorbs carbon dioxide and is converted back into bicarbonate solution. Thereafter, the bicarbonate solution 114 is returned from the contact medium 108 to the channels 104 to support further growth of the algae 32 therein.

Referring now to FIG. 3, a system for controlling the carbon enrichment of a media for growing an algae biomass in accordance with the present invention is shown and is generally designated 120. As shown, the system 120 includes a reactor 122 that may be of any type well known in the pertinent art, such as a standard plug flow reactor, an expanding plug flow reactor, or a pond. The system 120 also includes an absorber 124 and a power plant 126. In this combination, the reactor 122 and the absorber 124 are connected in fluid communication with each other. The power plant 126 is also connected in fluid communication with the absorber 124. As envisioned for the present invention, the power plant 126 is incorporated as a source of the combustion gases that are to be directed into the absorber 124. Further, the system 120 requires a controller 128 which will effectively control the flow of the media through the reactor 122 and through the absorber 124 for carbon enrichment of the media.

Still referring to FIG. 3, it will be seen that the reactor 122 has an input port 130 and an output port 132. Also, seen in FIG. 3 is that the absorber 124 has a media input port 134, a gas input port 136, a media output port 138 and a recycle output port 140. Interconnecting components in the system 120 include a sensor 142 that is positioned between the output port 132 of the reactor 122 and a pump 144. Specifically, the pump 144 is incorporated into the system 120 for the purpose of pumping media from the reactor 122 to the media input port 134 of the absorber 124 via a media flow line 146. In detail, the sensor 142 is positioned on the media flow line 146 for the purpose of measuring the carbon concentration level of media passing from the reactor 122 through the media flow line 146. For clarity the media flow line 146 is shown in FIG. 3 as a double line. Like sensor 142, a sensor 148 is shown positioned between the media output port 138 of the absorber 124 and the input port 130 of the reactor 122. Further, a recycle pump 150 can be included in the system 120 to establish a recycle flow line 152 between the recycle output port 140 of the absorber 124 and the media flow line 146 for fluid transfer back into the absorber 124 via the media input port 134 of the absorber 124.

As intended for the present invention, the carbon enrichment of the growth media is accomplished in the absorber 124. Referring now to FIG. 4, it will be seen that the absorber 124 includes a plurality of panels 154, with each panel 154 having an exposed surface 156. As shown, the media flow line 146 directs media into the absorber 124 through the media input port 134. Also, combustion gases 158 are directed from the power plant 126 into the absorber 124 through the gas input port 136. Thus, as media passes through the absorber 124 it is presented on the respective surfaces 156 of the plurality of panels 154. The resultant dispersion of media on the surfaces 156 then facilitates the capture of carbon by the media from the combustion gases 158 during a counter flow of the combustion gases 158 over the media on the surfaces 156 of respective panels 154. The result here is that when a carbon-poor media is introduced into the absorber 124 through the media input port 134, a carbon-enriched media will be returned to the reactor 122 via the media output port 138.

FIG. 5 presents a decision flow chart 160 in which action blocks 162 and 164 indicate that certain parameters and measurements are required by the controller 128 for an operation of the system 120. Specifically, FIG. 3 indicates that the sensor 142 monitors and measures the media flow line 146 to obtain a first carbon concentration level, $C_{1(measured)}$, of the media as it exits from the reactor 122 through output port 132. FIG. 3 also indicates that the sensor 148 monitors and measures a second carbon concentration level, $C_{2(measured)}$, of the media as it is discharged from the media output port 138 of the absorber 124 for introduction into the reactor 122 through the input port 130. Additionally, action block 162 of the decision flow chart 160 requires input for the controller 128 in the form of a first preset carbon concentration $C_{1(set)}$, and a second preset carbon concentration $C_{2(set)}$. In detail, the first preset carbon concentration $C_{1(set)}$ is based on an apparent carbon dioxide $CO_2$ concentration gradient that is determined by an interaction between aqueous media in the reactor 122 and the atmosphere of the local environment of the reactor 122. As envisioned for the present invention this local environment may include bicarbonate, carbonic acid or carbon dioxide. On the other hand, the second preset carbon concentration $C_{2(set)}$ is based on an apparent carbon dioxide $CO_2$ concentration gradient determined by an interaction between the combustion gases 158 from the power plant 126 and relatively carbon-poor growth media in the absorber 124. As stated above, both $C_{1(set)}$ and $C_{2(set)}$ are predetermined inputs to the controller 128.

Inquiry block 166 in FIG. 5 indicates that the pump 144 is to be activated to operate with a predetermined low fluid flow rate (see action block 168), when $C_{1(measured)}$ from sensor 142 is above (i.e. not below) $C_{1(set)}$. On the other hand, inquiry block 166 indicates that the pump 144 is to be activated to operate with a predetermined high fluid flow rate (see action block 170) when $C_{1(measured)}$ is below $C_{1(set)}$. In either case, inquiry block 172 indicates that the recycle pump 150 may be activated to recycle media (see block 174) whenever $C_{2(measured)}$ is below $C_{2(set)}$. The intended consequence of all this is that the system 120 is operated with an optimal transfer of carbon from the media for the production of a biomass 176 (see FIG. 3).

While the particular Controlled System for Supporting Algae Growth with Adsorbed Carbon Dioxide as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

What is claimed is:

1. A system for capturing carbon in a carbon-poor media to create a carbon-enriched media thereof, for assimilation of the carbon captured by the enriched media into an algae biomass, the system comprising:
    a reactor for growing algae biomass in the media, wherein the reactor has an input port and an output port;
    an absorber having a plurality of panels, wherein each panel has a surface area, and wherein the absorber has a first input port, a second input port, a first output port and a second output port;
    a source of combustion gases with a conduit for directing the combustion gases into the absorber through the first input port of the absorber;
    a pump for establishing a volumetric flow rate of carbon-poor media from the output port of the reactor and into the second input port of the absorber, wherein the carbon-poor growth media is presented on panel surface areas in the absorber for a counter current flow interaction with the combustion gases to create the carbon-enriched growth media for discharge from the first output port of the absorber and into the reactor through the input port of the reactor;
    a first sensor for measuring a first carbon concentration level, $C_{1(measured)}$, in the reactor at the output port of the reactor;
    a second sensor for measuring a second carbon concentration level, $C_{2(measured)}$, of media discharged from the first output port of the absorber; and
    a controller for operating the pump with input from the first and second sensors to establish an optimized assimilation of captured carbon from the carbon-enriched growth media into the algae biomass in the reactor.

2. A system as recited in claim 1 wherein a first preset carbon concentration $C_{1(set)}$ is based on an apparent carbon dioxide $CO_2$ concentration gradient determined by an interaction between aqueous media in the reactor and the atmosphere of the local environment of the reactor, wherein a second preset carbon concentration $C_{2(set)}$ is based on an apparent carbon dioxide $CO_2$ concentration gradient determined by an interaction between combustion gases and relatively carbon-poor growth media in the absorber, and further wherein $C_{1(set)}$ and $C_{2(set)}$ are predetermined inputs to the controller.

3. A system as recited in claim 2 wherein the pump is activated to operate with a predetermined high fluid flow rate when $C_{1(measured)}$ is below $C_{1(set)}$ and, alternatively, when $C_{2(measured)}$ is below $C_{2(set)}$, and further wherein the pump is activated to operate with a predetermined low fluid flow rate when $C_{1(measured)}$ is above $C_{1(set)}$.

4. A system as recited in claim 2 wherein a gaseous component of the local environment of the reactor is selected from the group consisting of bicarbonate, carbonic acid and carbon dioxide.

5. A system as recited in claim 1 wherein the reactor is selected from the group consisting of a pond, a plug flow reactor, and an expanding plug flow reactor.

6. A system as recited in claim 1 wherein the first sensor is located between the output port of the reactor and the second input port of the absorber.

7. A system as recited in claim 1 further comprising a recycling pump for transferring media from the second output port of the absorber and back into the absorber via the second input port of the absorber.

8. A system as recited in claim 7 wherein the recycling pump is activated to transfer media back into the absorber when $C_{2(measured)}$ falls below a predetermined value.

* * * * *